(12) United States Patent
Weill

(10) Patent No.: US 8,096,789 B2
(45) Date of Patent: Jan. 17, 2012

(54) SIMPLIFIED CLEANING AND FILLING DEVICE WITH A PISTON

(76) Inventor: David Weill, Begnins (CH)

( * ) Notice: Subject to any disclaimer, the term of this patent is extended or adjusted under 35 U.S.C. 154(b) by 785 days.

(21) Appl. No.: 11/629,326

(22) PCT Filed: Jun. 9, 2005

(86) PCT No.: PCT/IB2005/001611
§ 371 (c)(1),
(2), (4) Date: Dec. 11, 2006

(87) PCT Pub. No.: WO2005/120736
PCT Pub. Date: Dec. 22, 2005

(65) Prior Publication Data
US 2007/0235066 A1    Oct. 11, 2007

(30) Foreign Application Priority Data

Jun. 11, 2004    (FR) ..................................... 04 06332

(51) Int. Cl.
*F04B 7/04*    (2006.01)
*F04B 39/10*    (2006.01)
*F04B 35/02*    (2006.01)
*F04B 9/08*    (2006.01)

(52) U.S. Cl. ........................................ 417/490; 417/386

(58) Field of Classification Search .................... 433/81, 433/83, 89, 90, 224, 80, 82, 84, 85, 87; 134/104.2, 134/166 R, 169 R, 169 A, 195–196; 32/51, 32/54, 60, 56; 128/218; 222/251–415; 604/118–121, 128–129, 246–249, 30, 31, 604/33; 417/490, 501, 386, 388; 73/864.01; 422/100

See application file for complete search history.

(56) References Cited

U.S. PATENT DOCUMENTS

| | | | | |
|---|---|---|---|---|
| 3,816,922 A | * | 6/1974 | Thiel et al. ...................... | 433/83 |
| 3,990,152 A | * | 11/1976 | Hirdes ............................ | 433/89 |
| 4,021,921 A | * | 5/1977 | Detaille ......................... | 433/81 |
| 4,092,778 A | * | 6/1978 | Hirdes ............................ | 433/83 |
| 4,768,955 A | * | 9/1988 | Hirdes ............................ | 433/89 |
| 4,993,947 A | | 2/1991 | Grosrey | |
| 5,282,366 A | * | 2/1994 | Reilly et al. ................... | 62/292 |
| 5,295,828 A | | 3/1994 | Grosrey | |
| 6,030,215 A | * | 2/2000 | Ellion et al. ................... | 433/89 |
| 6,824,751 B2 | | 11/2004 | Rossell | |
| 2003/0103855 A1 | * | 6/2003 | Kim et al. ...................... | 417/501 |
| 2005/0221253 A1 | * | 10/2005 | Spinello ......................... | 433/33 |

FOREIGN PATENT DOCUMENTS

| | | | |
|---|---|---|---|
| DE | 198 48 479 A | 5/2000 | |
| EP | 0 299 919 A | 1/1989 | |
| EP | 0 538 200 A | 4/1993 | |
| EP | 0 521 119 B | 5/1996 | |

(Continued)

*Primary Examiner* — Todd Manahan
*Assistant Examiner* — Matthew Nelson
(74) *Attorney, Agent, or Firm* — Frommer, Lawrence & Haug LLP; Ronald R Santucci

(57) ABSTRACT

A device for difficult intervention in a closed enclosure, having an enclosure connected to the closed enclosure via a duct, a piston that can be moved by a motor, a geometry allowing a contact with the outside air when the piston occupies a certain position within the enclosure in order to generate a sudden release of pressure, and an outlet valve remaining closed when the piston increases the volume of the enclosure so as to cause the pressure reduction within the enclosures.

16 Claims, 7 Drawing Sheets

| | FOREIGN PATENT DOCUMENTS | |
|---|---|---|
| JP | 2003119867 | 4/2003 |
| WO | WO 92/12685 | 8/1992 |
| WO | WO 95/35069 | 12/1995 |
| WO | WO 00/45859 | 8/2000 |

* cited by examiner

SIMPLIFIED CLEANING AND FILLING DEVICE WITH A PISTON

This application is a 371 of PCT/IB2005/001611 filed on Jun. 9, 2005, published on Dec. 22, 2005 under publication number WO 2005/120736 A1 which claims priority benefits from French Patent Application Number 04/06332 filed Jun. 11, 2004.

The invention relates to a method and a device for a filling, cleaning, unblocking-type intervention in a closed or virtually closed enclosure. It is particularly suitable for complex-shaped and/or hard-to-reach cavities. It offers many applications including in construction, chemical or food production installations, medicine and dentistry.

BACKGROUND OF THE INVENTION

To clean a closed enclosure, it is known practice to make two openings in the enclosure in order to cause a fluid, gaseous or liquid, where necessary having chemical cleaning properties, to circulate therein at high pressure. This method rapidly reaches its limits:
  for certain complex shapes of the enclosure, walls remain unreachable by the fluid and uncleaned;
  in addition, simple circulation requires a relatively long cleaning time and generally represents mediocre effectiveness.

To fill an air-filled closed or semi-closed cavity with a liquid or pasty substance, it is known practice to connect a water inlet duct in an opening of the cavity and to provide a discharge of the air, either through a second opening or through the same opening. Such a method is however lengthy if the volume is great. In addition, it does not make it possible to perfectly fill a cavity whose shape is complex, has thin and narrow ramifications, in which air pockets remain trapped.

DESCRIPTION OF THE PRIOR ART

Such a filling solution is described in document EP0538200 in the dental field, for which the closed enclosure is the inside of a tooth that has to be filled with a filler paste. This solution consists in a mechanism for aspirating the volume of the tooth allowing it to be filled at the same time with a paste. Such a method has the disadvantages of a lengthy filling if the volume is great, of not allowing a filling of all the interstices of the cavity and residual air pockets remaining trapped.

A second solution in the dental field is described in document U.S. Pat. No. 4,021,921. This solution consists in inserting a liquid inside a tooth with the aid of a pump pushing the liquid. This solution also provides for the addition of gas bubbles and the use of pressure oscillations combined with periodic pulses, applied via a control of the pump allowing it to carry out repeated start and stop cycles. This solution has the advantage of improving the cleaning and filling effect that would be obtained by a simple circulation of pressurized liquid. However, the proposed device has the disadvantage of being complex, of having a voluminous mechanism and of being difficult to apply and to control due to the particular operation of the pump. Additionally, the solution does not make it possible to fully eliminate all the air pockets from the cavity and its filling and cleaning are insufficient.

A third solution in the dental field is described in document EP0299919. This solution is based, on the one hand, on a pump which makes it possible to create a vacuum in the tooth and on a device with a piston which has the function of inserting into the tooth a pressurized cleaning liquid. This device operates on the basis of the cavitation phenomena, of which the high energy involved makes it possible to resolve the disadvantages of the preceding solutions. However, such a solution requires two controlled pumping systems, relatively long ducts, many connections, depends on the inertia of the components in motion, the inertia of the columns of liquids in motion and is subjected to the various damping factors associated with the various components such as the ducts in the context of the pressure variations. This solution relies therefore on a complex mechanism posing problems of reliability. In addition, the energy consumed is considerable and this solution causes a considerable consumption of liquid. Finally, it generates cavitation phenomena that are always accompanied by often undesirable violent effects and are not suitable for the envisaged uses. A variant of this solution, which has the same disadvantages, is described in document EP0521119.

A solution having similar disadvantages is described in document EP0766535.

Another solution using cavitation is described in document EP1146914. It consists in the creation of a low pressure by a device that is periodically placed in contact with the enclosure to be cleaned, in alternation with a setting at atmospheric pressure. This solution is based on a rotor rotated by a motor and containing several internal ducts to connect the various pressure sources to the cavity of the closed enclosure. This device has many disadvantages like those mentioned previously, to which the fact of using the rotor is added: specifically, this device requires particular connections between the ducts, causes losses of energy and wear by friction, problems of sealing and hygiene because the liquid passes through the rotor.

When a duct is blocked, it is known practice to try to unblock it by filling it, for example, with water according to the preceding technique hoping that the pressure will be sufficient to clear the blockage. In practice, this method is limited in the case of stubborn blockages.

SUMMARY OF THE INVENTION

A general object of the invention consists in proposing a method and a device that allow a difficult intervention of the cleaning, filling, unblocking type in a hard-to-reach closed cavity.

More precisely, the object of the invention is to propose a method and a device suitable for filling, cleaning, unblocking-type operations that make it possible to obtain a good result and in a short time.

An object of the invention also consists in proposing a method and a device suited to different fields such as construction, chemical or food installations, the cavity being able to be a liquid-conveying duct or a tank, or such as the medical and dental field, the cavity being able to be an artery or a tooth.

An object of the invention consists in proposing a simple method and device, of little bulk and low cost.

The concept of the invention consists in subjecting the enclosure, within which the intervention is necessary, to cycles of sudden pressure releases, causing a particular motion of fluid, gaseous, liquid and even pasty, within the enclosure, which has the effect of cleaning, filling, unblocking the enclosure.

More precisely, the device according to the invention for difficult intervention in a closed enclosure comprises an enclosure connected to the closed enclosure via a duct, a piston that can move thanks to a motor, a geometry allowing a contact with the outside air when the piston occupies a certain position within the enclosure in order to generate a sudden release of pressure, and an outlet valve remaining closed when the piston increases the volume of the enclosure so as to cause the pressure reduction within the enclosures.

The motor may consist of a pneumatic device, comprising a closed enclosure comprising a gas inlet and outlet, a piston connected to the piston of the enclosure.

The device may also comprise a spring opposing the motor and allowing the movement of the piston in a first direction, the motor causing the movement of the piston in a contrary direction.

The enclosure of the device may comprise a hole, a groove or a sectional enlargement to place its volume in contact with the outside and cause a sudden release of pressure when the piston reaches a certain position.

The device may comprise a duct of which one end is designed to penetrate within the enclosure, and of which the other end is connected to a fluid reservoir.

It may comprise a cone made of silicone or elastomer traversed by the end of the tube or tubes designed to penetrate within the closed enclosure, the cone being adapted to its positioning in an opening of this closed enclosure. One of the ducts may protrude by a greater length from the cone in order to penetrate more deeply within the closed enclosure.

The invention also relates to a method for difficult intervention in a closed enclosure in contact with the enclosure of the device via a duct, comprising a repetition of the following steps:
- a motor pushes a piston in the direction of reducing the volume of the enclosure, the pressure of the enclosures remaining constant under the effect of an open outlet valve,
- the motor pulls the piston in the opposite direction so as to increase the volume of the enclosure, the valve being closed, which causes the pressure reduction within the enclosures,
- sudden release of pressure within the enclosures by placing the enclosure of the device in contact with the outside air when the piston reaches a geometry of the enclosure.

The device and method of the invention may be used to clean and fill a tooth or a bone.

DESCRIPTION OF THE DRAWINGS

These objects, features and advantages and others of the present invention will be explained in detail in the following description of particular embodiments given on a nonlimiting basis in relation to the appended figures amongst which.

DESCRIPTION OF THE PREFERRED EMBODIMENTS

Figure 1:
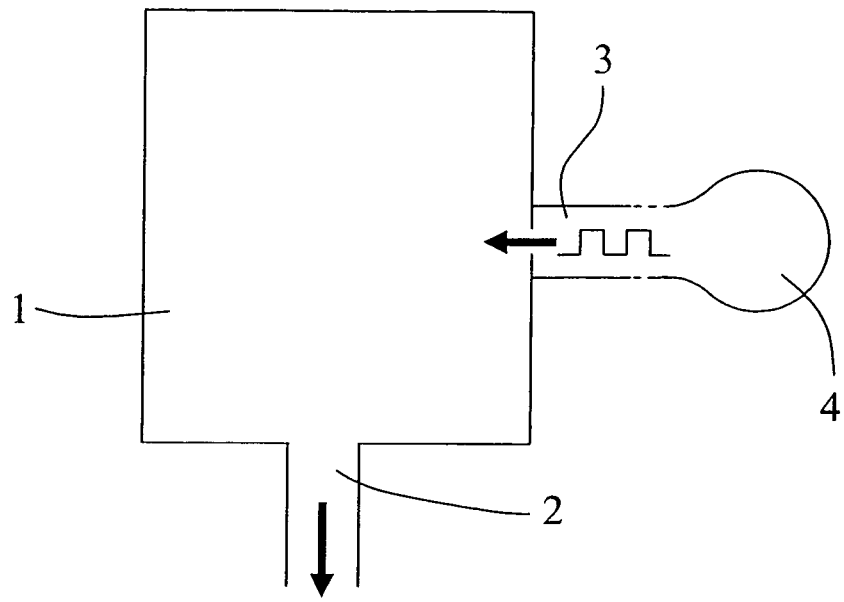
FIG. 1 represents a schematic view illustrating the concept of the invention.
Figure 2:
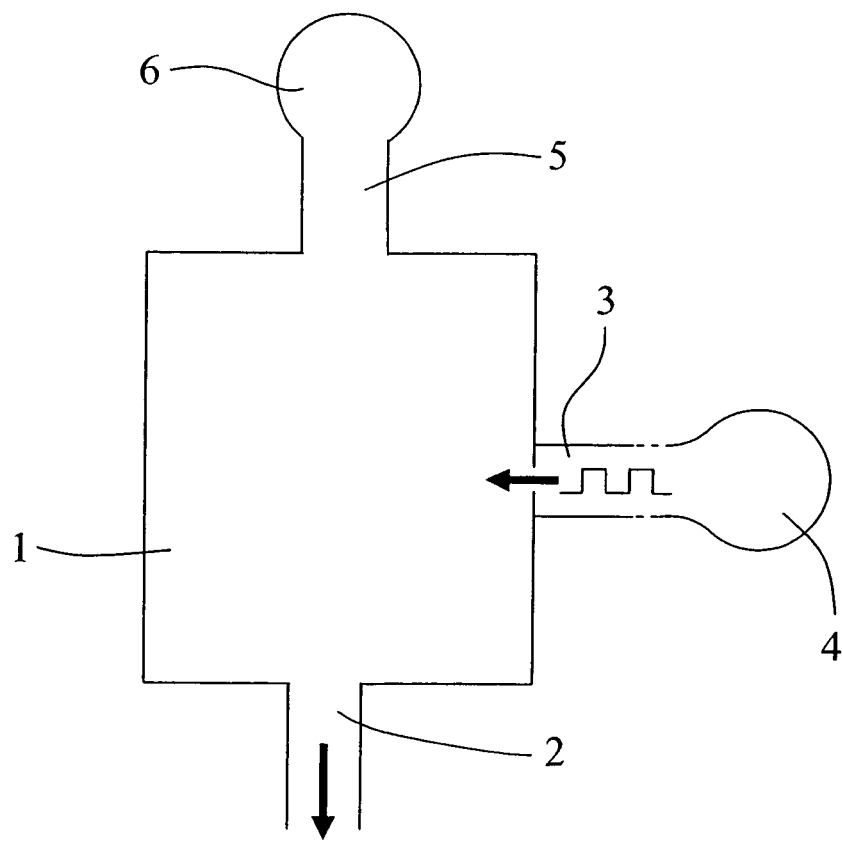
FIG. 2 represents a schematic view of a variant of a device according to the concept of the invention.
Figure 3:
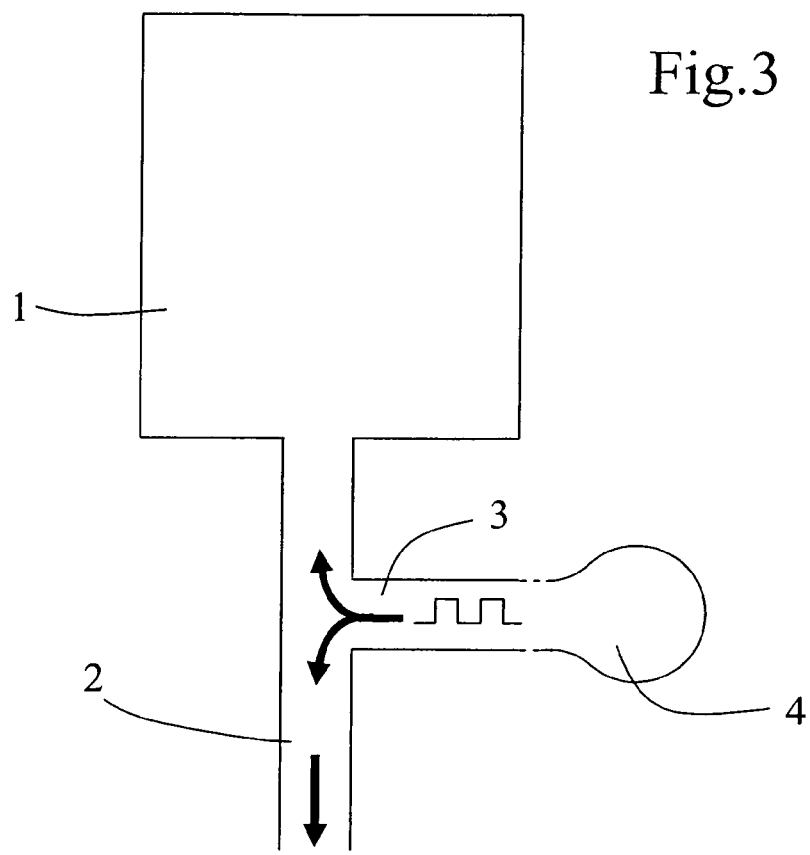
FIG. 3 represents a variant of the diagram of FIG. 1.

FIGS. 1 to 3 represent schematic devices illustrating the concept of the invention.

FIG. 1 illustrates a closed cavity 1 on which it is necessary to intervene, for a cleaning operation. The device according to the invention comprises a pressure reduction means 2 connected to the cavity via a first opening, this means being a pump in this embodiment, a means of sudden pressure release 3 connected to the enclosure 1 via a second opening, this means being a valve-type release device in this embodiment and this means being connected to a reservoir containing a fluid 4, air at atmospheric pressure in this embodiment.

For reasons of simplification, the cavity is represented schematically as rectangular. It could however have any complex form and particularly have hard-to-reach nooks.

The cleaning method of the invention, applied with the aid of the foregoing device, comprises the following essential steps:
- reduction of the pressure inside the enclosure 1 with the aid of the suction pump 2 which sucks out the air present in the enclosure;
- below a certain threshold pressure, sudden release caused by the valve 3, which consists in the sudden inrush of the air 4 into the enclosure and causes the sudden pressure increase inside the enclosure.

The foregoing steps are repeated cyclically.

The pressure reduction means 2 may be of a mechanical type such as a pump, of the hydraulic type, such as a turbine, of the electromechanical type, such as a vibration pump whose operating cycle is sufficiently high to be considered continuous. It operates in a continuous or virtually continuous manner so that it causes a virtually permanent flow of air within the enclosure.

The release device 3 has the function of causing a sudden pressure increase, and may consist in a simple device suddenly placing the enclosure at low pressure in contact with the outside at constant pressure, such as the air at atmospheric pressure for example. It may consist in a simple mechanical device consisting of a ball blocking off an opening of the enclosure and connected to a spring, this ball being able to be moved so as to release the opening of the enclosure when the pressure difference between the inside and the outside of the enclosure reaches a sufficient value to oppose the force of the spring. This device may also be based on the constant elasticity of a material that makes it possible to open a valve when the pressure reduction exceeds a certain threshold. This phenomenon causes a sudden change in the virtually permanent flow. As a variant, this device may be controlled, the valve being mechanically controlled for example.

The combination and repetition of the two foregoing effects make it possible to create a circulation of air marked by violent movements inside the enclosure which makes it possible to obtain a better cleaning than with a simple flow.

This device may also be used with any fluid 4. Note that in the case of a liquid such as water, by nature incompressible, such a device remains effective by the fact that there always remain at least a few air bubbles within the enclosure, a phenomenon due to the imperfect geometry of the walls of the enclosure, to the possible presence of polluting products, solid or liquid, at the openings for example, which allows the device to produce the pressure cycle described hereinabove. According to the concept of the invention, the extreme conditions of cavitation are not sought and are not necessary, unlike the prior art. However, the invention remains compatible with these extreme conditions and nothing would prevent the device from operating in such conditions if certain applications required it.

FIG. 2 represents a schematic view of a variant embodiment. In this variant, the device includes additionally a means 5 of supplying a fluid 6, water in this embodiment, through a third opening in the enclosure 1. The supply means may be a simple duct connected to a water reservoir at a certain pressure, advantageously high and constant.

This device makes it possible to carry out the following steps:
- reduction of the air pressure inside the enclosure 1 with the aid of the suction pump 2 which sucks out the air present in the enclosure;
- in parallel, filling of the enclosure with the water originating from the supply means 5, this filling being promoted by the pressure of the water at the inlet and by the suction via the means 2;
- below a certain threshold pressure, sudden release caused by the valve 3, which consists in the sudden inrush of the air 4 into the enclosure and causes the sudden pressure increase inside the enclosure.

Note that this device makes it possible to obtain the following effects:
- the release of air inside the enclosure creates an impact inside the enclosure, that is transmitted into the volume of the enclosure by the water due to its virtually incompressible character;
- without any particular priming method, the enclosure finishes by being filled with water, this filling being better than in the case of a simple supply of water. Specifically, this device makes it possible to reach any corners of the enclosure, under the effect of the sudden releases;
- nevertheless, there always remain a few gas bubbles which allow the suction then release mechanism to continue operating even when the enclosure is almost entirely full of water. These air bubbles are of very small size and often invisible to the naked eye at atmospheric pressure. They may move at random with the sudden convection movements generated by the releases and they have a volume which increases with the pressure reduction, this volume variation also being able to be an additional source of convection movement in the liquid. Thanks to these phenomena, the gas bubbles actively participate in the cleaning of the surfaces;
- the cleaning effect within the enclosure is very effective.

Finally, this device makes it possible to combine the action of two complementary fluids, the air which allows a mechanism of pressure reduction then sudden release, and the water, with, where necessary, an addition of liquid cleaning product, which may have a more effective cleaning effect than the air alone, and participates effectively in the transmission of the shock waves. Naturally, any other combination of fluids, liquid, gaseous and even pasty, is possible, as is the use of a liquid comprising solid particles in suspension.

This device and method therefore make it possible to obtain improved cleaning. It is possible to exploit the principles of the invention in a secondary application to clean an object that is positioned in the enclosure.

In addition, they make it possible to fill the enclosure 1 well with water. Finally, this system is also perfectly suited to the unblocking of the enclosure, due to the fact that filling is improved and makes it possible to reach zones that are difficult to reach with a simple flow, and due to the fact that the sudden pressure reductions make it possible to transfer impacts that have a positive effect on the unblocking action.

FIG. 3 represents schematically a variant of the device of FIG. 1, which has the advantage of requiring only a single opening in the enclosure 1 to use the functions of pressure reduction and sudden pressure release. Specifically, in this case, the pressure release device 3, in the form of a valve, is connected to an opening of the outlet duct of the pressure reduction mechanism.

Figure 4:
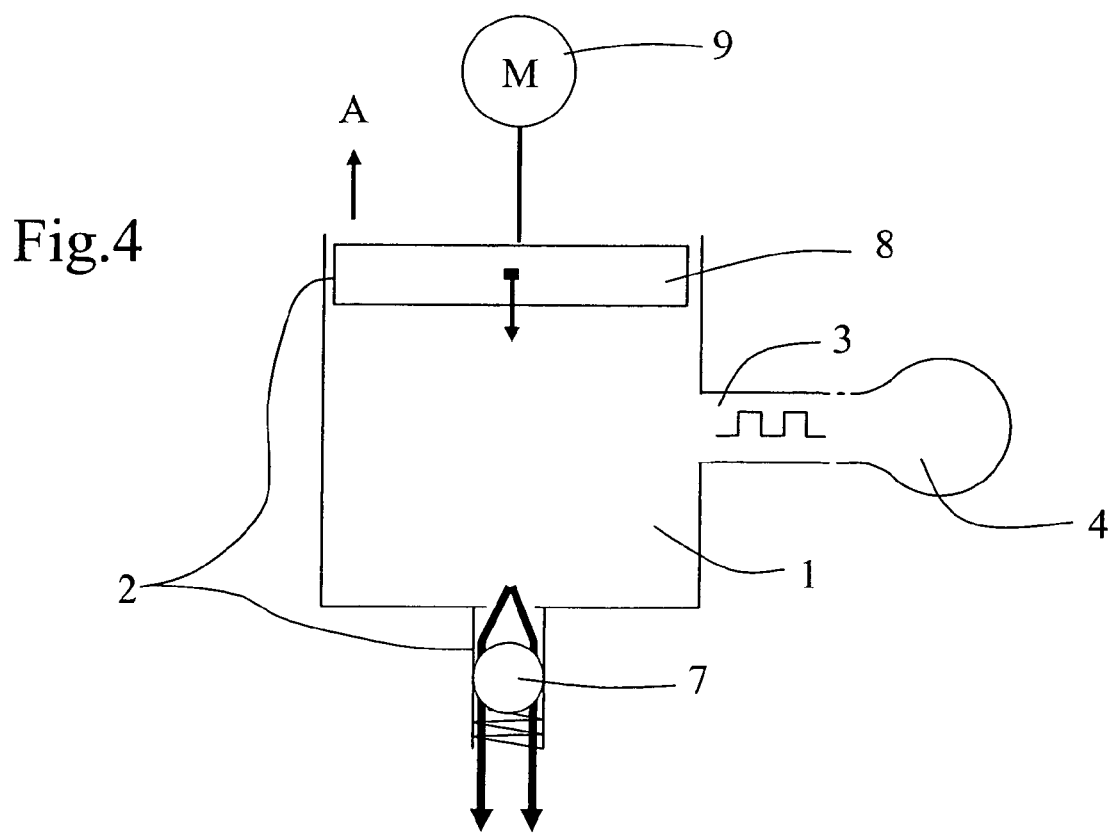
FIG. 4 represents an embodiment with piston.

FIG. 4 represents schematically an embodiment of the mechanism of FIG. 1. This device comprises an outlet valve 7 connected to the enclosure 1 via a first opening, a release device 3 as described previously. The enclosure comprises an open part closed by a piston 8, this piston being able to be set in motion in the direction of the arrow A or in the contrary direction with the aid of a motor 9.

This device operates as follows:
- according to a first phase, the motor 9 pushes the piston 8 in the direction contrary to the arrow A, which causes the discharge of the air from the enclosure via the valve 7, the pressure of the enclosure remaining constant;
- then the motor 9 sets the piston in motion in the direction of the arrow A, which has the effect of reducing the pressure of the enclosure, the valve 7 remaining closed in this phase;
- beyond a certain value of this pressure, the device 3 causes a sudden release within the enclosure, which causes a sudden increase in the pressure and the filling of the enclosure with air.

It is therefore evident that this device makes it possible to use the method of the device of FIG. 1, described hereinabove.

In this embodiment, the pressure reduction method consists in an outlet valve 7, a piston 8 and a motor 9.

Figure 5A:
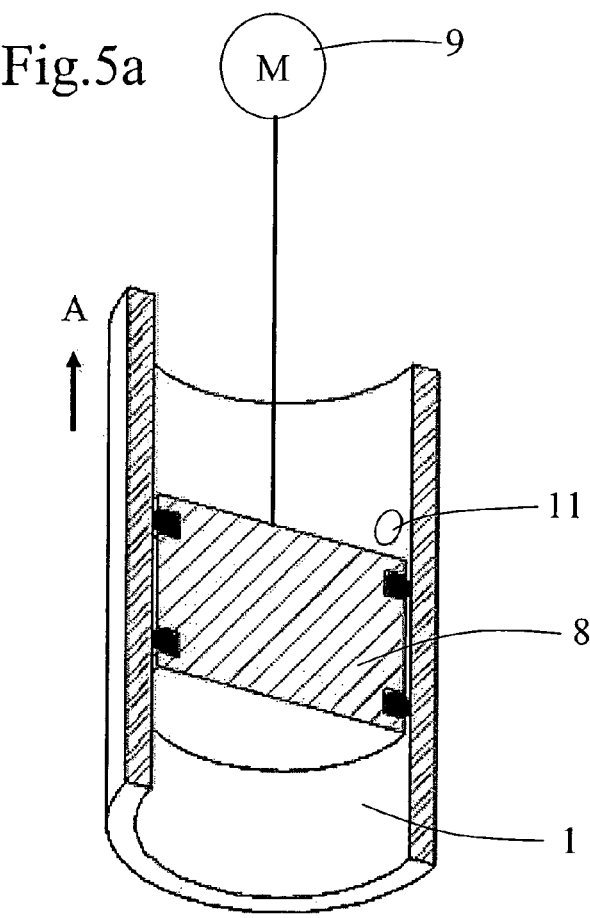
FIGS. 5a to 5c are variant embodiments of the means of sudden release of pressure.
Figure 5B:
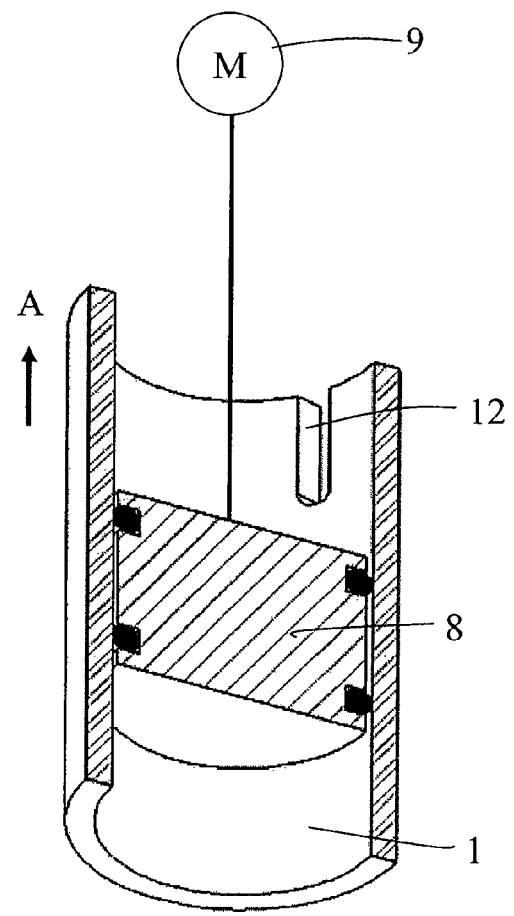
Figure 5C:
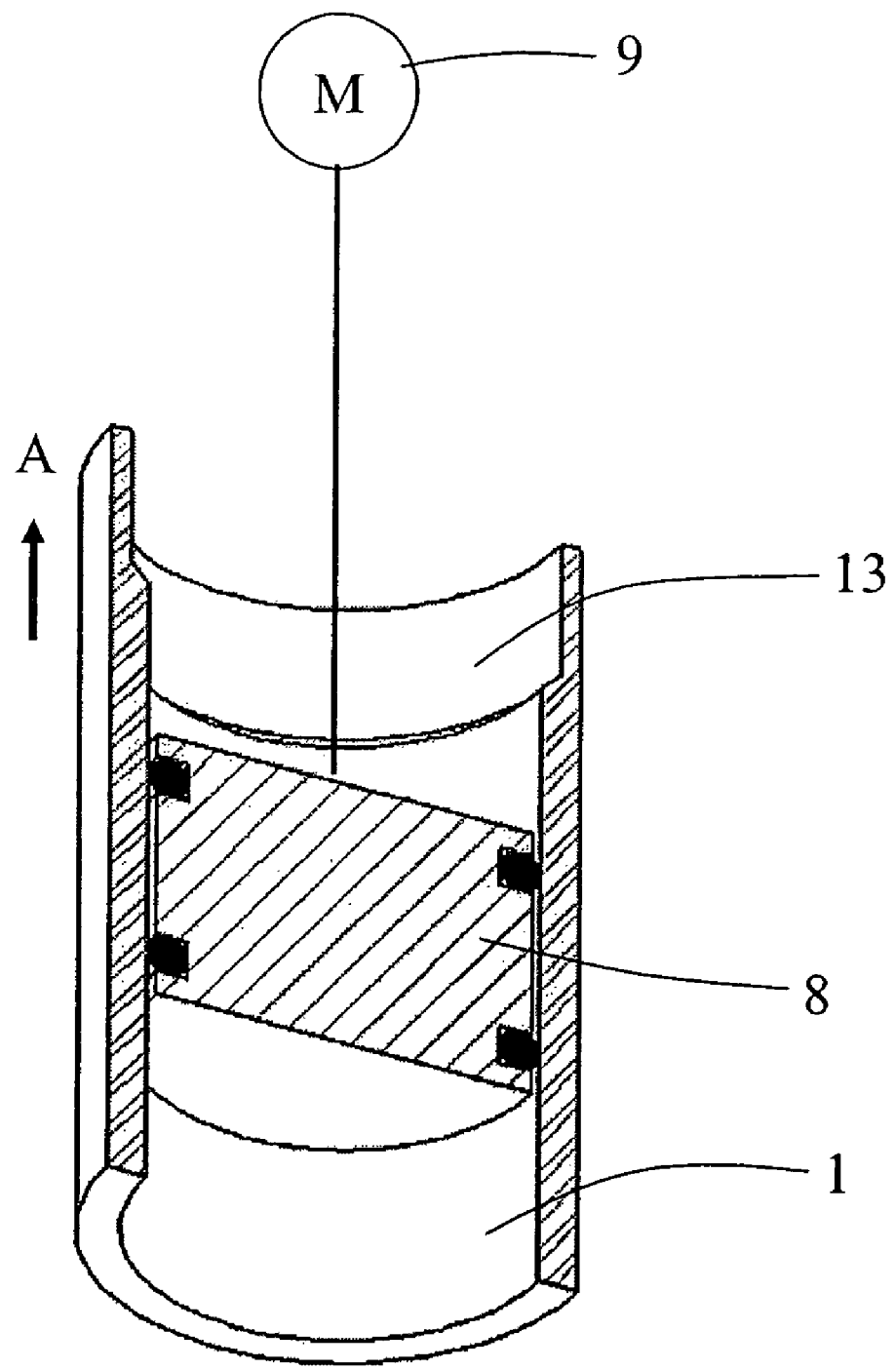

FIGS. 5a to 5c represent variant embodiments of the device of FIG. 4, with simplified sudden pressure release devices.

Specifically, FIG. 5a represents in section a cylindrical enclosure in which a hole 11 is made in its wall, allowing a contact with the air at atmospheric pressure. In this device, when the piston, which moves in the direction of the arrow A causing the enclosure 1 to be placed at low pressure, reaches a position in which it is beyond the hole 11, the enclosure at low pressure is suddenly placed in contact with the outside air at atmospheric pressure, which causes the sudden release effect. Thus, the sudden pressure release device is filled by the combination of the piston 8 and the hole 11 in this device.

As a comment, this device combines the two functions of pressure reduction 2 and of sudden release 3 by means of the piston 8, which makes it a controlled system, unlike the preceding devices in which the two means operated independently.

The device of FIG. 5b represents a variant in which the hole 11 is replaced by a groove 12.

The device of FIG. 5c represents a variant in which the hole 11 is replaced by an enlargement 13 of the cross section of the enclosure, which allows the air to pass at the sides, via the space that lies between the wall of the enlarged enclosure and the piston.

Figure 6:
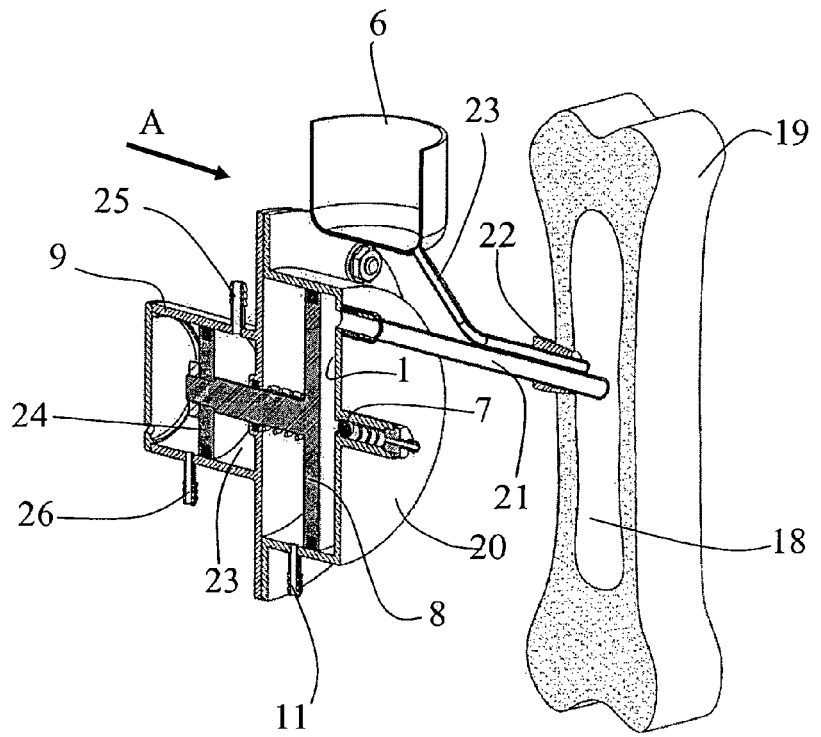
FIG. 6 represents a device according to the invention in a medical application.

FIG. 6 represents another variant of a device of the invention, in an application for cleaning the inside of a bone and then filling it with a resin. This device is based on the principles set out schematically in FIGS. 4 and 5.

Since it is not possible to place a piston directly in contact with the interior volume 18 of a bone 19 to be cleaned and filled, a particular device 20 is used. This device comprises a cylindrical enclosure 1, connected to the cavity 18 of the bone through a duct 21 penetrating into the bone through an opening 22, the seal being provided by the use of a cone pushed into the opening and allowing the ducts to pass through. This cone may be made of elastomer or silicone, is retained by simple wedging, the pressure reduction inside the bone also participating in keeping it in place.

This device comprises a piston 8, set in motion by a pneumatic motor 9 and a spring 10. The piston 8 occupies a sufficient cross section of the enclosure 1 to make it possible to cause pressure variations within it with its movement. The device also comprises a valve 7 and an opening 11 in its wall, the assembly having been described in relation to FIG. 4. Finally, a duct 23 for supplying fluid 6 is also connected to the cavity 18 of the bone via the opening 22. The enclosures 18 and 1 are at the same pressure and thus represent the equivalent of a single enclosure, which makes it possible to apply the previously described methods.

This device has an embodiment in which the motor 9 is a pneumatic system, based on an enclosure 23 affixed to the enclosure 1 in a sealed manner, including a piston 24 connected to the piston 8, an air inlet 25 and an air outlet 26. Naturally, it is possible to symmetrically exchange the directions of setting in motion of the motor 9 and of the spring 10.

The pistons 8 and 24 and the enclosures 1 and 23 are dimensioned to obtain the pressure variations and forces necessary to each application.

This motor may be replaced by any other equivalent system or combination of means, such as springs, electric motors, etc.

Figure 7A:
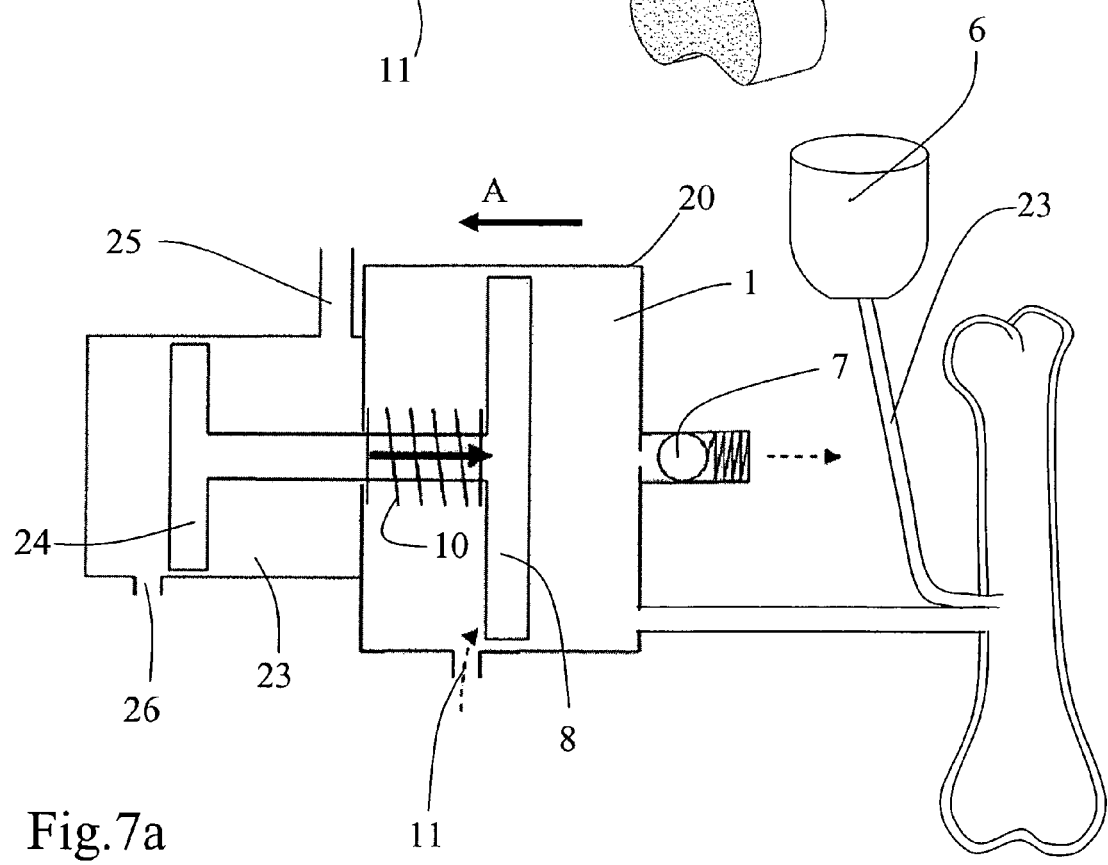
FIGS. 7a to 7c illustrate the operation of the device of FIG. 6.
Figure 7B:
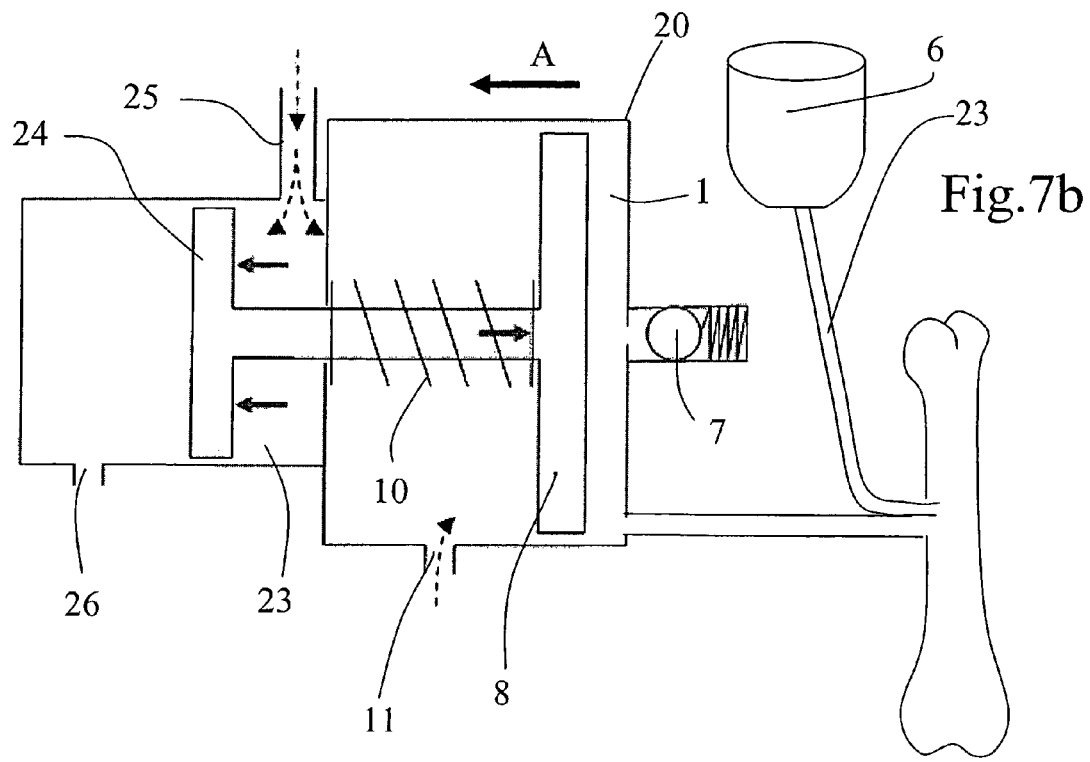
Figure 7C:
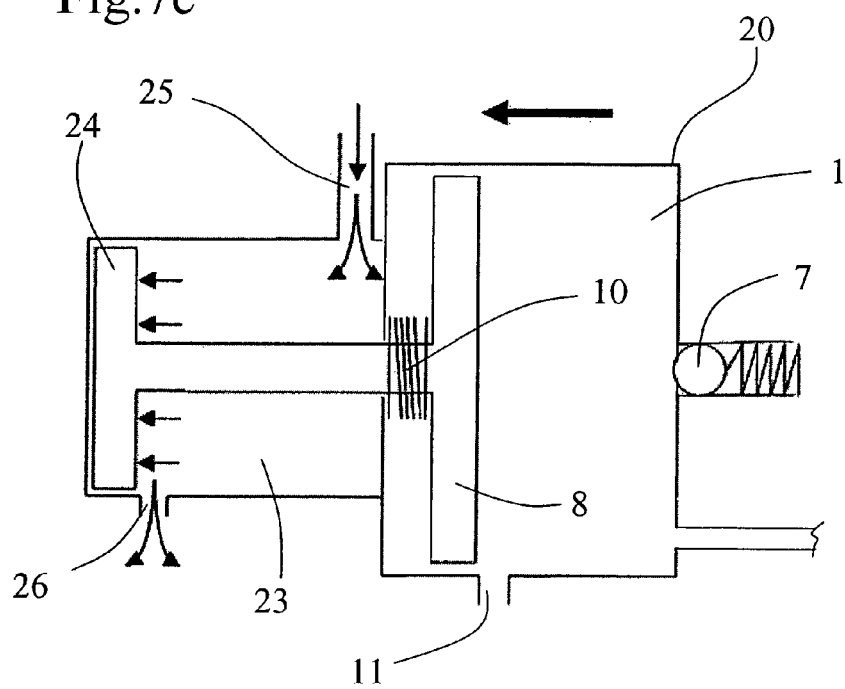

FIGS. 7a to 7c illustrate the operation of the device.

In FIG. 7a, the piston is midway in the cavity 1 of the device 20. The spring 10 exerts a force which pushes the piston in the direction contrary to the arrow A. The device is such that, in this phase, the pressure force of the spring is greater than the opposite pneumatic force exerted on the piston 8 by the piston 24 under the pressure of the air entering via the inlet 25. This movement of the piston causes air to exit via the outlet valve 7, the pressure of the enclosure 1 remaining constant.

At the end of travel of the piston 8, represented in FIG. 7b, the air pressure on the piston 24 in the chamber 23 is sufficient to oppose the force of the spring 10 and the piston begins a travel in the direction of the arrow A. During this movement, the valve 7 now remaining closed, the air pressure reduces in the enclosure 1. At the same time, the enclosure fills with fluid 6.

When the piston 8 reaches the position represented in FIG. 7c, the enclosure 1 is suddenly in contact with the outside by means of the opening 11, which causes the sudden inrush of air through the opening 11 since the enclosure 1 is at low pressure. At the same time, the enclosure 23 is designed so that the position of the piston 24 releases the outlet opening 26 of the chamber 23, which allows the pressurized air to escape from the enclosure 23 and the pneumatic force exerted on the piston 24 to reduce sharply, thus again becoming less than the force of the compressed spring 10. The movement of the piston in the direction contrary to the arrow A recommences.

The cycles succeed one another in this way, causing pressure reductions and sudden pressure releases within the enclosures 1 and 18.

These cycles may first be carried out with a supply of water, the reservoir 6 being filled with water, in order to clean the cavity 18, then the water may be replaced by resin and the cycles resumed until the cavity 18 is satisfactorily filled with resin. Note that this device makes it possible to obtain both a surprising cleaning and filling, in a very short time.

This device makes it possible, on the one hand, to clean the cavity 18 of the bone with the aid of a cleaning fluid 6. It also makes it possible to fill this cavity with a paste, by putting it in the place of the cleaning fluid.

Figure 8:
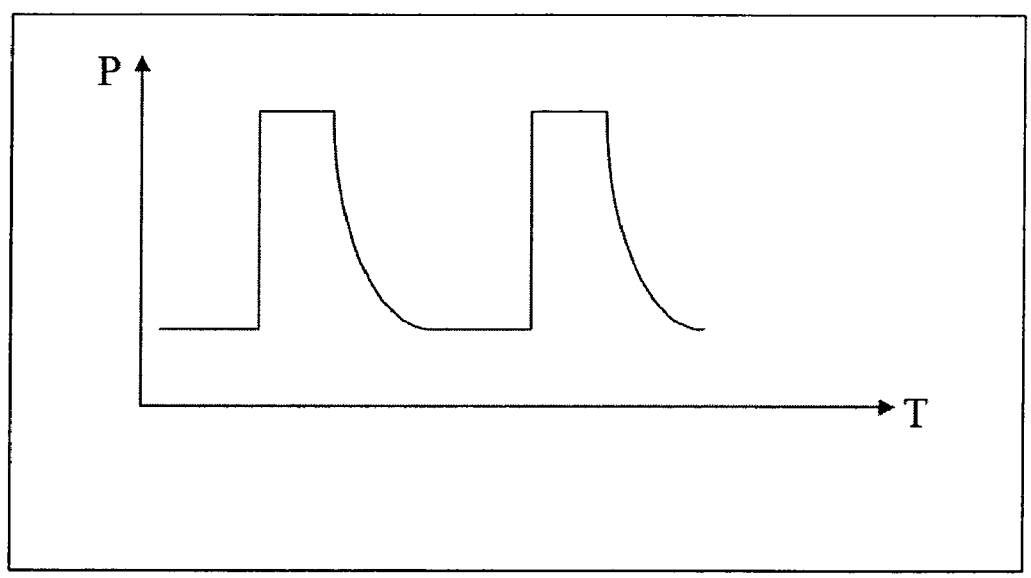
FIG. 8 represents the pressure curve as a function of the time obtained with the device of FIGS. 4 to 6.

This device makes it possible to achieve the pressure curve shown in FIG. 8 within the cavity 1. In a first phase, corresponding to FIG. 7a, the pressure remains constant and equal to atmospheric pressure. In a second phase, corresponding to FIG. 7b, the pressure reduces progressively and in the third phase, corresponding to FIG. 7c, the pressure suddenly rises again, that is to say in a very short time, to atmospheric pressure.

Those skilled in the art will adapt the device to suit it to the different fields of application mentioned hereinabove.

As an additional comment, this device can function in other particular conditions in which there is a change of state of a fluid, in which there are cavitation phenomena. It remains compatible with the addition of complementary components such as pressure sensors, devices such as a transducer in contact with the fluid or submerged in the cavity in order to add complementary vibratory and/or thermal phenomena, of the ultrasound type for example.

The device and method of the invention finally have the following advantages:
  it is suitable for various fields of application;
  it makes it possible to achieve very good cleaning, filling, unblocking performance in a short time;
  it is highly simplified, low cost, can be discarded after one use, which is very advantageous in, for example, the medical and dental fields whose requirements in hygiene terms are very considerable;
  it is not very bulky and can be very easily connected to outside ducts and to a cavity to be treated;
  it operates only with a simple supply of gas and, where necessary, a supply of fluid. It does not require a large amount of energy.
  it is primed only by its filling properties.

The invention claimed is:

1. A device for difficult intervention in a closed enclosure, the device comprising:
  an enclosure adapted to be connected to a closed enclosure via a duct such that the enclosure and the closed enclosure are always at the same pressure,
    wherein the enclosure comprises:
      a piston adapted for movement by a motor, and
    wherein the enclosure comprises:
      a particular geometry allowing a contact with the outside air when the piston occupies a certain position within the enclosure in order to generate a sudden increase of pressure, and
    wherein the device comprises:
      an outlet valve remaining closed when the piston increases the volume of the enclosure so as to cause the pressure reduction within the enclosures.

2. The device as claimed in claim 1, wherein the motor is a pneumatic device.

3. The device as claimed in claim 2, wherein the pneumatic motor comprises a closed enclosure comprising a gas inlet, a piston connected to the piston of the enclosure and a gas outlet.

4. The device as claimed in claim 1, which also comprises a spring opposing the motor and allowing the movement of the piston in a first direction, the motor causing the movement of the piston in a contrary direction.

5. The device as claimed in claim 1, wherein the enclosure comprises a hole to place its volume in contact with the outside and cause a sudden release of pressure when the piston reaches a certain position.

6. The device as claimed in claim 1, wherein the enclosure comprises a groove to place its volume in contact with the outside and cause a sudden release of pressure when the piston reaches a certain position.

7. The device as claimed in claim 1, wherein the enclosure comprises a sectional enlargement to place its volume in contact with the outside and cause a sudden release of pressure when the piston reaches a certain position.

8. The device as claimed in claim 1, which comprises a duct of which one end is designed to penetrate within the enclosure, and of which the other end is connected to a fluid reservoir.

9. The device as claimed in claim 8, which comprises a cone made of silicone or elastomer traversed by the end of the duct or ducts designed to penetrate within the closed enclosure, the cone being adapted to its positioning in an opening of the enclosure.

10. The device as claimed in claim 9, wherein one of the ducts protrudes by a greater length from the cone in order to penetrate more deeply within the closed enclosure.

11. A method for difficult intervention in a closed enclosure, with the exception of closed enclosures which are parts of the human body, and hence with the exception of surgical methods applied to the human body, in contact with the enclosure of a device as claimed in claim 1 via a duct, which comprises a repetition of the following steps:
- a motor pushes a piston in the direction of reducing the volume of the enclosure, the pressure of the enclosures remaining constant under the effect of an open outlet valve,
- the motor pulls the piston in the opposite direction so as to increase the volume of the enclosure, the valve being closed, which causes the pressure reduction within the enclosures,
- sudden release of pressure within the enclosures by placing the enclosure in contact with the outside air when the piston reaches a geometry of the enclosure.

12. The method for difficult intervention in a closed enclosure, with the exception of closed enclosures which are parts of the human body, and hence with the exception of surgical methods applied to the human body, as claimed in claim 11, wherein the motor consists of a motor operating in only one direction, the movement of the piston in the other direction being implemented by a spring.

13. The method as claimed in claim 11, which comprises, in parallel with the preceding steps, a step of supplying the enclosure with fluid.

14. A device for difficult intervention in a closed enclosure, the device comprising:
- an enclosure adapted to be connected to a closed enclosure via a duct, such that the enclosure and the closed enclosure are always at the same pressure,
  - wherein the enclosure comprises:
  - a piston adapted for movement by a motor, and
  - wherein the enclosure comprises:
  - a particular geometry allowing a contact with the outside air when the piston occupies a certain position within the enclosure in order to generate a sudden increase of pressure in the enclosure and the closed enclosure, and
- wherein the device comprises:
  - an outlet valve remaining closed when the piston increases the volume of the enclosure so as to cause the pressure reduction within the enclosures, and remaining open when the piston reduces the volume of the enclosure, so that the pressure in the enclosures remains constant.

15. A device for difficult intervention in a closed enclosure, the device comprising:
- an enclosure linked to a duct adapted to be connected to a closed enclosure such that the enclosure and the closed enclosure are always at the same pressure,
  - wherein the enclosure comprises:
  - a piston adapted for movement by a motor, and
  - wherein the enclosure comprises:
  - a particular geometry allowing a contact with the outside air when the piston occupies a certain position within the enclosure in order to generate a sudden increase of pressure in the enclosure and the closed enclosure, and
- wherein the device comprises:
  - an outlet valve not placed in between the duct and the enclosure, remaining closed when the piston increases the volume of the enclosure so as to cause the pressure reduction within the enclosures.

16. A device for difficult intervention in a closed enclosure, the device comprising:
- an enclosure linked to a first duct adapted to be connected to a closed enclosure such the enclosure and the closed enclosure are always at the same pressure,
  - wherein the enclosure comprises:
- a piston adapted for movement by a motor, and
  - wherein the enclosure comprises:
- a particular geometry allowing a contact with the outside air when the piston occupies a certain position within the enclosure in order to generate a sudden increase of pressure in the enclosures, and
  - wherein the device comprises:
- an outlet valve, remaining closed when the piston increases the volume of the enclosure so as to cause the pressure reduction within the enclosures,
  - wherein the device comprises:
- a second duct, distinct from the first duct, having a first end adapted to penetrate within the enclosure, and a second end connected to a fluid reservoir, distinct from the outside air.

* * * * *